United States Patent [19]

Beard et al.

[11] Patent Number: 5,020,790
[45] Date of Patent: Jun. 4, 1991

[54] POWERED GAIT ORTHOSIS

[75] Inventors: John E. Beard; Franklin L. Spillman, both of Baton Rouge, La.; Oscar Banos, Dallas, Tex.; David Showers, Monroe; John M. Fussell, Bogalusa, both of La.; George LeBlanc, N. Palm Beach, Fla.

[73] Assignee: Board of Supervisors of Louisiana State University and Agricultural and Mechanical College, Baton Rouge, La.

[21] Appl. No.: 602,003

[22] Filed: Oct. 23, 1990

[51] Int. Cl.⁵ .......................... A61F 2/60; A61F 2/64; A61F 2/70
[52] U.S. Cl. .................................. 272/70; 128/80 R; 128/80 F; 623/24; 623/27; 901/12
[58] Field of Search ............. 128/80 R, 80 F; 272/70; 901/12, 19; 623/24, 27, 39

[56] References Cited

U.S. PATENT DOCUMENTS

| | | | |
|---|---|---|---|
| 2,210,269 | 8/1940 | Taylor | 128/80 R |
| 2,573,866 | 11/1951 | Murphy | 128/80 F |
| 4,557,257 | 12/1985 | Fernandez et al. | 128/80 F |

FOREIGN PATENT DOCUMENTS 464768  5/1950  Canada .................... 623/27

Primary Examiner—Richard J. Apley
Assistant Examiner—Karen G. Horowitz
Attorney, Agent, or Firm—Notaro & Michalos

[57] ABSTRACT

An orthosis for powering the walking movement of a paralyzed wearer, comprises torso members to be firmly connected to the opposite sides of the wearer's torso. A pair of leg braces is connected to the torso members. Each leg brace comprises a thigh member pivotally mounted at a hip joint to one torso member on one side of the wearer. A shank member connected to the shank and foot of the wearer, is pivotally mounted at a knee joint to each thigh member. A four link drive mechanism which is powered by a rechargeable power unit mounted on the torso member, swings the thigh member forwardly and rearwardly about the hip joint. A knee lock keeps the knee joint locked during the rearward movement of the thigh member and during a portion of the forward movement of the thigh member. At an appropriate point during the forward movement of the thigh member, a cam operated crank unlocks the knee joint and swings the shank member rearwardly to simulate a natural forward step. As the thigh member reaches its maximum forward position, a return spring pulls the shank member forwardly until it is substantially parallel to the thigh member. At this point, the knee joint is again locked and the wearer's foot strikes the ground. This begins the rearward swinging of the thigh member which propels the wearer's torso forwardly to complete the step. The opposite knee brace is then operated in an analogous fashion to execute a second step.

17 Claims, 4 Drawing Sheets

POWERED GAIT ORTHOSIS

FIELD AND BACKGROUND OF THE INVENTION

The present invention relates in general to devices for helping individuals to walk, and in particular to a new and useful orthosis which can produce walking movements in the legs of a paraplegic.

In the United States, there are approximately 250,000 paraplegics. The main causes of paraplegia are spina bifida, muscular dystrophy, and accidents.

In addition to the obvious result of paraplegia, namely the loss of an individual's ability to walk, the paraplegic suffers additional physiological and psychological damage, due to the fact that the individual is constantly lying down or sitting. The physiological problems include deterioration of muscles, bones and some organs. The psychological problems include the fact that the paraplegic must always look up at others. This is particularly distressing and demoralizing to small children.

A variety of solutions have been proposed to overcome the foregoing problems.

One of these solutions is a simple brace which can hold the paraplegic in an upright standing position. This device is marketed under the trade name Parapodium, by the firm of Durr-Fillaur. The Parapodium is nothing more than a fixed pedistal which provides no ambulatory capacity to the wearer.

Other solutions are also known which utilize driven or non-driven, articulated braces to aid in the walking of paraplegics, amputees and other persons with impaired walking ability.

U.S. Pat. No. 1,351,955 to Lowry discloses a battery and motor driven knee joint for swinging the lower leg portion of a full leg prosthesis, to the rear around an artificial knee joint, to simulate a normal walking movement for the artificial leg. The wearer is assumed to have one fully functional natural leg.

U.S. Pat. No. 2,010,482 to Cobb discloses a drive orthopedic brace which is meant to be strapped to the two legs of a crippled person. A crank near the hip is rotated for driving the leg braces to produce a walking movement. The crank rotates a pair of cam mechanisms which alternately swing the upper leg portions of the brace. With each swinging movement, lower stirrups engaged under the feet of the wearer are drawn upwardly to shorten the effective length of the leg and produce a more natural walking movement. Except for strapping the upper and lower legs of the wearer to upper and lower leg portions of the braces, no special mechanism is provided for insuring a correct bending of the knee during the walking operation.

U.S. Pat. No. 2,573,866 to Murphy discloses full leg braces for a paraplegic which have both hip and knee joints with automatic releases for simulating the correct articulation of the legs during a walking movement. Power is provided by the paraplegic who shifts his or her weight from side to side with the aid of crutches which are used in conjunction with the braces. While the knee joints can be released during each step, and this may reduce the amount of so called "hip tuck" movement which is required for braces having locked knees, no mechanism is provided in this reference for powering the rearward swinging of the lower leg. "Hip tuck" movement is required for manipulating the reciprocating gait orthosis of U.S. Pat. No. 4,697,808 to Larson et al., for example, which shows another walking aid.

U.S. Pat. No. 2,210,269 to Taylor discloses a rolling carriage having a complex linking mechanism for artificially producing leg and foot articulation to aid in the rehabilitation of patients suffering from motor loss of the lower limbs, for example motor loss due to infantile paralysis.

SUMMARY OF THE INVENTION

The present invention comprises a set of braces for the legs of a user, which form an articulated exoskeleton for the user. The braces include a torso member which is meant to be fixed securely to the torso of the wearer. The torso member forms a first link for each leg portion of the brace for defining a frame of reference for the rest of the brace. A second link which carries a cam, is mounted for rotation to each of the torso members. A rechargeable battery operated motor and gear box rotate each cam and link combination. The second link is included in a four link mechanism connected to a thigh member which is firmly engaged to the thigh of the wearer. Rotation of the second link causes the upper leg portion of the wearer to swing forwardly to initiate a step. At the same time, a cam follower which is engaged to the cam, activates a cable mechanism which releases a knee lock and thereafter pulls a shank or lower leg member rearwardly. The shank member is pivotally connected to the thigh member at a knee joint. The rearward movement of the shank member is synchronized with the forward movement of the thigh member to simulate the taking of a natural step. When the forward movement of the thigh member is completed, the shank member is extended to relock the knee joint, as the leg of the wearer strikes the ground. The second link then powers the rearward swinging of the thigh member. This moves the torso of the wearer forwardly to complete the step. The sequence is then repeated for the opposite leg brace.

Accordingly, another object of the present invention is to provide a powered gait orthosis, comprising: a torso member for connection to the torso of a wearer; a thigh member connected at a hip joint to the torso member for connection to the thigh of the wearer; a shank member connected at a knee joint to the thigh member for connection to the shank of the wearer; hip drive means connected to the thigh member for pivoting the thigh member forwardly and rearwardly on the hip joint with respect to the torso member; knee drive means connected to the shank member for pivoting the shank member rearwardly on the knee joint with respect to the thigh member, the hip and knee drive means being operatively engaged with each other for simulating the taking of a natural step by the wearer; and an automatic knee joint lock operatively connected between the thigh member and the shank member for locking the knee joint, the knee joint lock being connected to the knee drive means for unlocking the knee joint in synchronism with activation of the knee drive means to allow the shank member to pivot on the knee joint.

Another object of the present invention is to provide a powered gait orthosis which is simple in design, rugged in construction and economical to manufacture.

The various features of novelty which characterize the invention are pointed out with particularity in the claims annexed to and forming a part of this disclosure. For a better understanding of the invention, its operat-

DESCRIPTION OF THE PREFERRED EMBODIMENT

Figure 1:
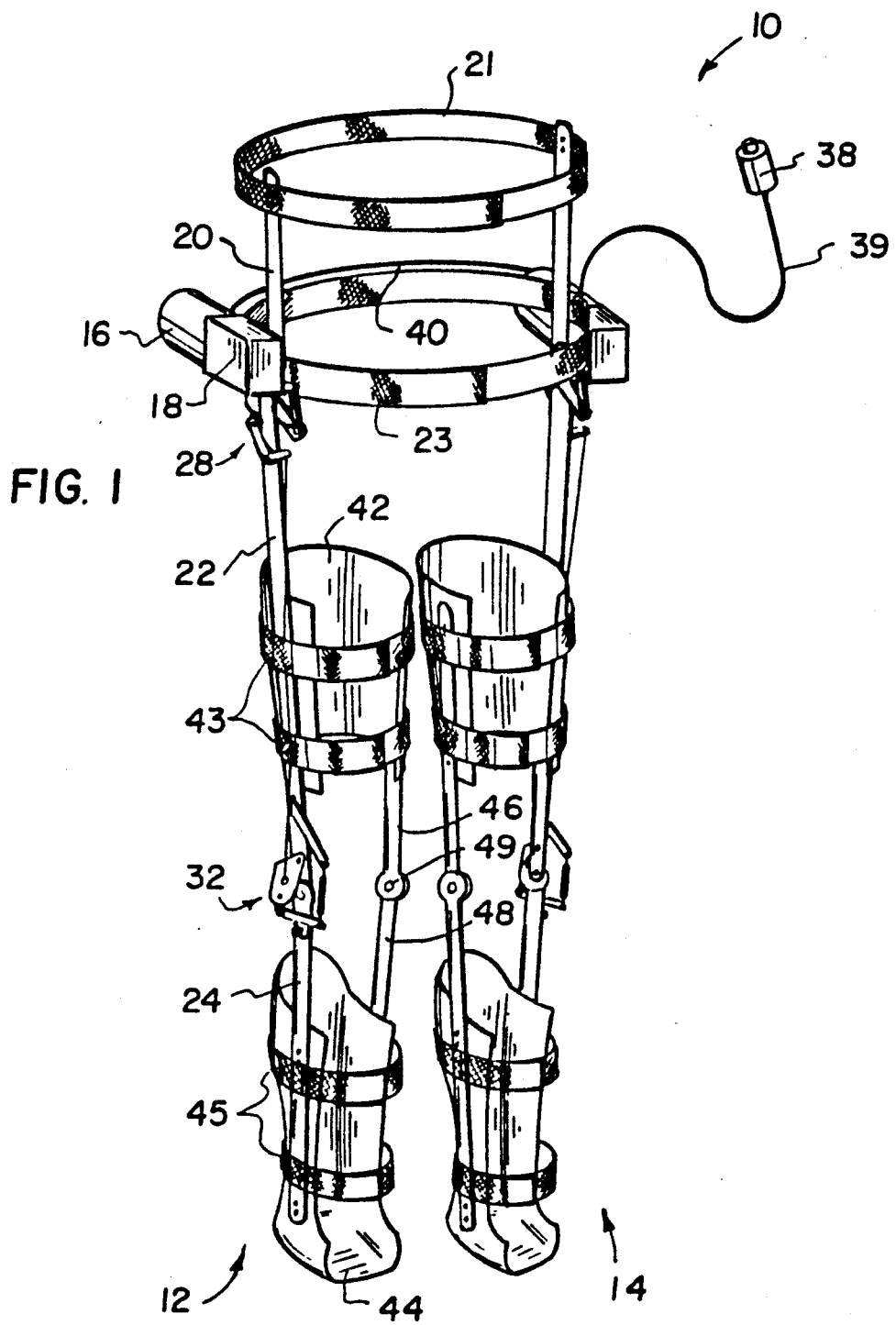
FIG. 1 is a perspective view of the powered gait orthosis in according with the present invention.

Referring to the drawings in particular, the invention embodied in FIG. 1 comprises a powered gait orthosis generally designated 10 having a pair of leg braces generally designated 12 and 14 which are connected to the torso and legs of a wearer (not shown).

The left leg brace 14 is a virtually identical mirror image of the right leg brace 12 so that only the right leg brace will be described in detail.

Power for the leg brace is provided by a power unit which is mounted on a torso member 20. A pair of torso members are strapped to the opposite sides of the wearer's torso by a chest strap 21 and a waist strap 23.

The power unit comprises a rechargeable battery driven motor 16 and a gear box 18 connected to the motor. The inventors have found that a working example of the present invention can be achieved by utilizing a combination battery and motor assembly available in the Black & Decker, Professional Cordless Drill. The gearbox was taken from a Black & Decker Sheet Metal Nibbler.

Driving circuitry is provided in each power unit for synchronizing the alternate movement of the leg braces 12 and 14. This movement is continued as long as a dead man switch 38 is depressed. Switch 38 is connected by an electrical cable 39 to one of the power units which are connected to each other by second electrical cable 40. If switch 38 is released, both power units are deactivated.

The right leg brace 12 further comprises hip drive means 28 which are connected to a thigh member 22 which is pivotally connected at a hip joint to the torso member 20. Thigh member 22 is securely connected to the thigh of a wearer by a flexible plastic thigh shell 42 and thigh straps 43.

A shank member 24 is pivotally mounted at a knee joint to the lower end of thigh member 22. Knee drive means 32 are connected between the thigh member and the shank member. A flexible plastic shank and foot shell 44 is securely connected to the shank and foot of the wearer by shank straps 45.

A passive thigh member 46 is pivotally connected at a passive knee joint 49 to a passive shank member 48. Member 46 is secured to shell 42 and member 48 is secured to shell 44 for bracing the inner surface of the wearer's leg.

Figure 2:
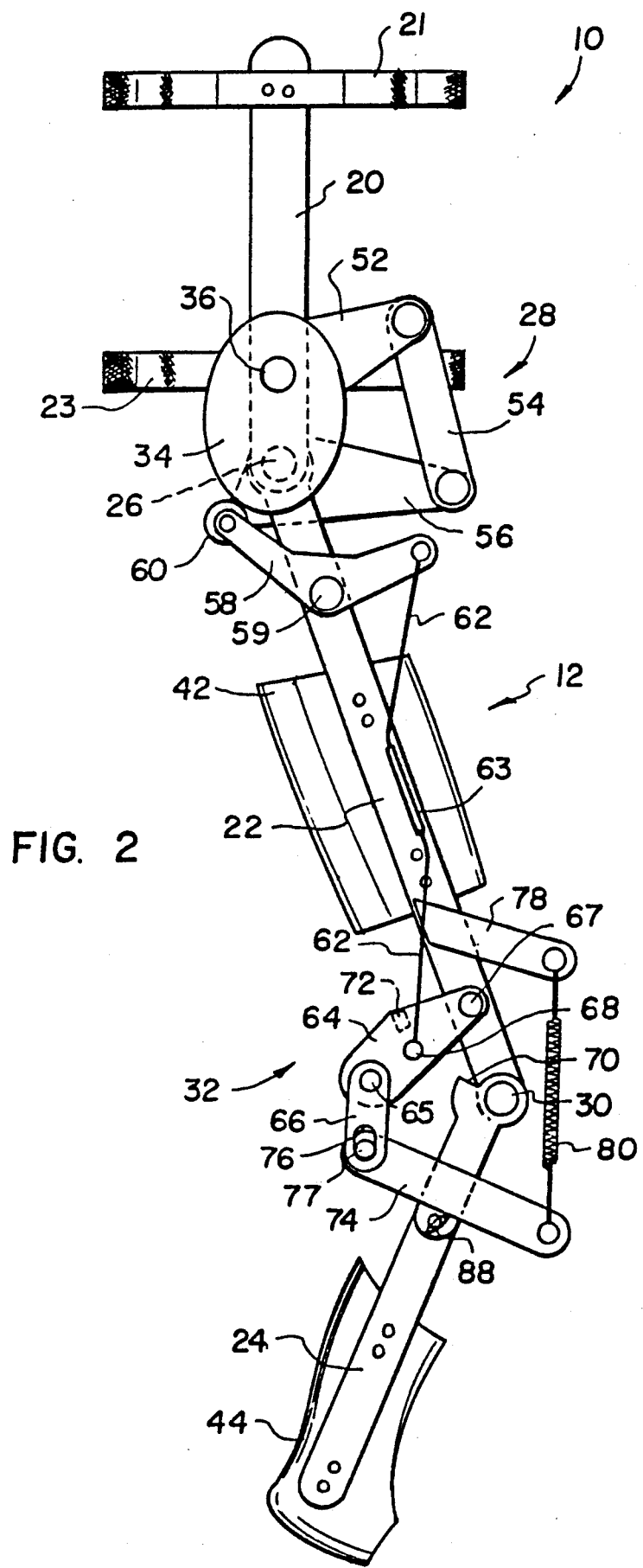
FIG. 2 is a side elevational view of the orthosis shown in FIG. 1, in an intermediate configuration during the taking of a step.
Figure 4:
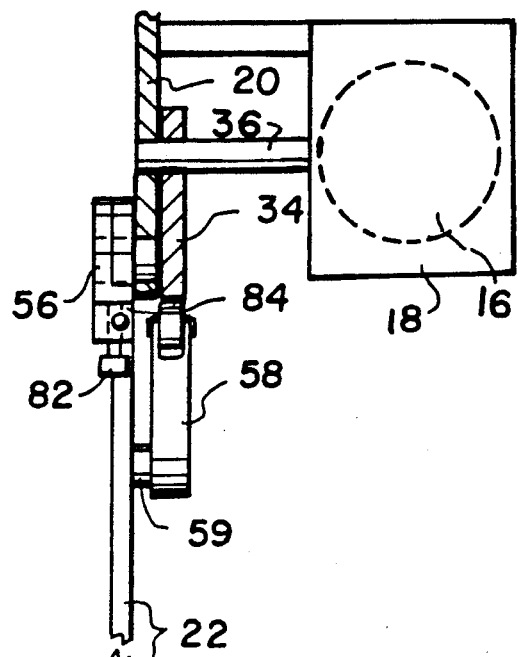
FIG. 4 is a fragmentary front elevational view of the orthosis, partially in section.
Figure 4:
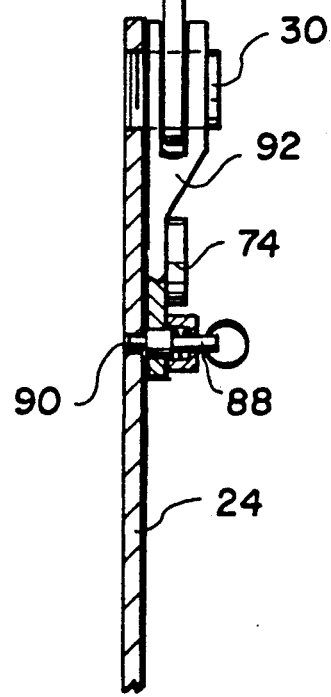

As best shown in FIGS. 2 and 4, gearbox 18 includes a drive shaft 36 which is rigidly connected to a cam 34 which rotates 360° with shaft 36. Shaft 36 is journaled for rotation within torso member 20 to establish a fixed relationship between the rotation axis of cam 34 and the torso member 20.

Hip drive means 28 comprise a four link drive for pivoting the thigh member 22 forwardly and rearwardly about the hip pivot joint 26, with respect to the torso member 20. The hip drive means include a second link 52 which is rigidly connected to the cam 34. A third link 54 is pivotally connected at one end to the free end of second link 52. A fourth link 56 is pivotally connected to the other end of third link 54 and is rigidly connected to thigh member 22. When cam 34 and second link 52 rotates 360° about the axis of drive shaft 36, thigh member 22 executes a first forwardly and then rearwardly swinging movement to a total of approximately 42°.

While this movement alone is capable of generating walking movement, the wearer must execute a hip tucking action so as to lift each foot at the end of each step by upward pivoting of the hip.

To avoid the need for this unnatural movement, the present invention utilizes knee drive means 32 which incorporate means for automatic locking and unlocking the knee joint.

Power is transmitted to the knee drive means by a rocker arm 58 which is pivotally mounted to thigh member 22 at a pivot pin 59. A roller 60 rotatably mounted to one end of arm 58 acts as a cam follower by rolling on the outer surface of cam 34. The rotation of cam 34 causes back and forth rocking movement of rocker 58 which alternatively pulls and releases a cable 62 which is guided through a cable holder 63 fixed to thigh member 22. The opposite end of cable 62 is connected at a cable connection 68 to a crank 64 pivotally mounted at pivot pin 67, near the lower end of thigh member 22. With cam 34 rotating counter clockwise, rocker 58 rotates in the same direction to pull cable 62 and lift crank 64, clockwise around pivot pin 67. This movement lifts a floating link 66 which is pivotally mounted at pivot 65 to crank 64. The lower end of link 66 carries an elongated slot 76 which receives a pin 77 fixed to the end of a shank lever 74. When crank 64 rotates clockwise, link 66 is lifted which in turn pulls on the rear end of shank lever 74, pivoting shank member 24 clockwise and to the rear around knee joint 30 with respect to thigh member 22. Shank member 24 is pivoted to its maximum extent as the thigh member 22 reaches its maximum forward position with respect to torso member 20. At this point cam 34 rotates beyond its top-dead-center position, allowing rocker 58 to rotate clockwise. Crank 64 is then rotated counterclockwise by a return spring 80 which is engaged between a thigh lever 78 fixed to thigh member 22, and the forward end of shank lever 74. The biasing of spring 80 causes shank member 24 to straighten to a fully extended and parallel position with respect to thigh member 22, and to bring crank 64 into a locked position shown in FIG. 3. This happens approximately at the same time that the wearer's foot strikes the ground.

The knee is locked by engagement of a knee lock projection 72 on the inner surface of crank 64, against a lock shoulder 70 defined on the upper end of shank member 24 adjacent the knee joint 30. The knee lock thus formed prevents flexing of the knee joint until crank 64 is once more pulled by cable 62 during a subsequent step.

The initial step is completed as the thigh member 22 swings to the rear of hip joint 26, propelling the wearer's torso forwardly.

The free pivotal movement of crank 64 and link 66 is insured by the elongated slot 76 which allows some lost movement between crank 64 and shank lever 74.

In order to allow the wearer to sit, it is necessary to disengage both the hip and the knee drive mechanisms.

Figure 3:
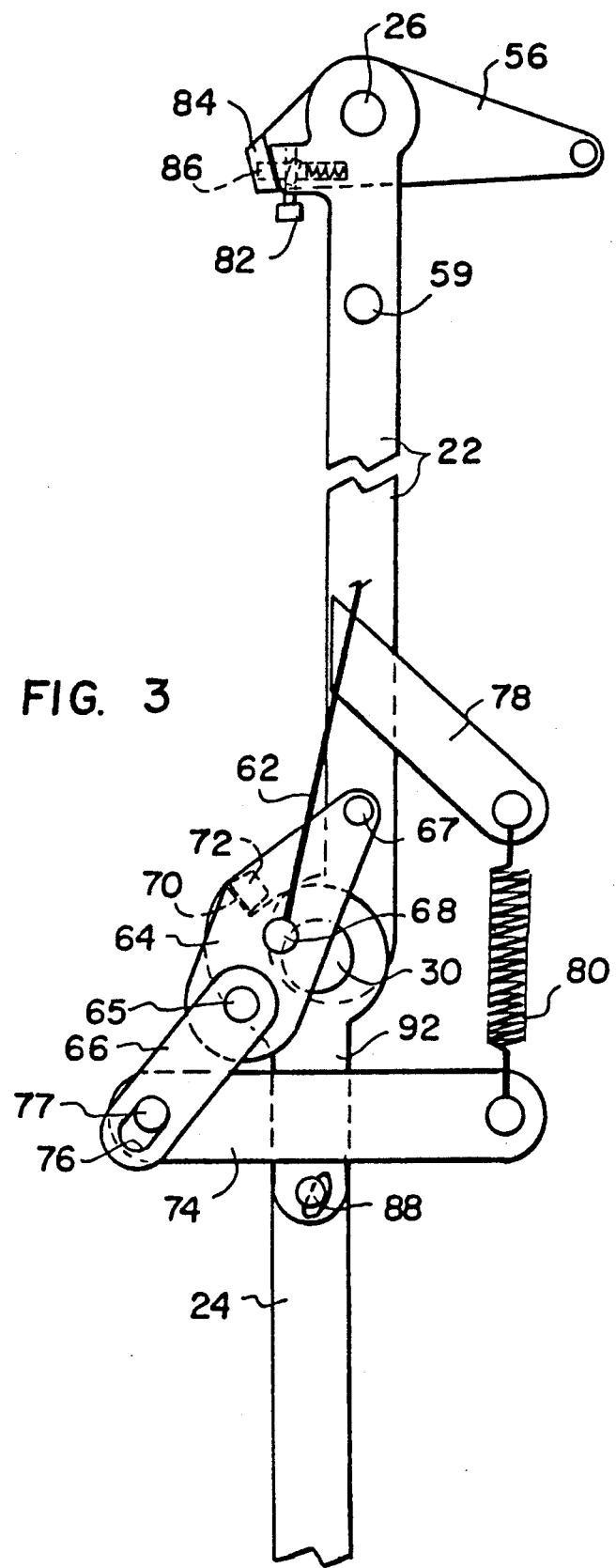
FIG. 3 is a fragmentary view showing parts of the driving and locking mechanisms for the hip and knee portions of the orthosis, in locked conditions.

The hip drive mechanism is disengaged by pushing upwardly on a hip release button 82 shown in FIGS. 3 and 4. A ramp surface is defined on the shank of push button 82 which engages a slot in a spring loaded locking pin 86 which is slidably mounted in the end of thigh member 22. Upward movement of hip release button 82 as shown in FIG. 3, causes pin 86 to move to the right, disengaging pin 86 from a bore in a hip lock projection 84 defined on the rear end of the fourth link 56. In this way fourth link 56 is mechanically disconnected from thigh member 22, allowing thigh member 22 to pivot freely about hip joint 26, to permit the wearer to bend at the waist and thus assume a sitting position.

At this point the wearer must manually disconnect the knee drive mechanism by pulling knee release pin 88 outwardly with the aid of a ring connected to the pin. As best shown in FIG. 4, the spring loaded pin 88 has an end which extends into a hole 90 in the shank member 24. Movement of pin 88 to the right as shown in FIG. 4, retracts the pin from hole 90, releasing the shank member 24 for free pivotal movement about the knee joint 30. Pin 88 and shank lever 74 are mounted on a forked shank release portion 92 which is also pivotally mounted on knee joint 30, so that the knee drive mechanism remains connected and intact despite the free pivotal movement of shank movement 24.

In this way, the knee joint 30 is released to allow the paraplegic to flex at the knees and sit in a normal fashion.

While a specific embodiment of the invention has been shown and described in detail to illustrate the application of the principles of the invention, it will be understood that the invention may be embodied otherwise without departing from such principles.

What is claimed is:

1. A powered gait orthosis, comprising:
   a torso member for connection to the torso of a wearer;
   a hip joint connected to said torso member;
   a thigh member connected at said hip joint to said torso member, for connection to the thigh of the wearer;
   a knee joint connected to said thigh member;
   a shank member connected at said knee joint to the thigh member, for connection to the shank of the wearer;
   motor driven hip drive means located on said torso member and connected to the thigh member for pivoting said thigh member forwardly and rearwardly on the hip joint with respect to the torso member;
   knee drive means connected between said hip drive means and said shank member for pivoting said shank member rearwardly on the knee joint with respect to the thigh member, the hip and knee drive means being operatively engaged with each other for simulating the taking of a natural step by the wearer; and
   an automatic knee joint lock operatively connected between the thigh member and the shank member for locking the knee joint, said knee joint lock being connected to the knee drive means for unlocking the knee joint in synchronism with activation of the hip drive means and the knee drive means to allow the shank member to pivot on the knee joint.

2. A powered gait orthosis according to claim 1, wherein said hip drive means comprises a four link drive, the torso member forming a first link of the four link drive, the four link drive including a second link mounted for rotation to the first link, power means connected to the second link for rotating the second link with respect to the first link, the four link drive including a third link pivotally connected to the second link and a fourth link rigidly connected to the thigh member and pivotally connected to the third link whereby rotation of the second link causes swinging forward and rearward movement of the thigh member about the hip joint.

3. A powered gait orthosis according to claim 2, wherein said knee drive means comprises a cam fixedly connected to the second link for rotation with the second link, a cam follower movably connected to the thigh member and engaged against the cam for rocking movement with rotation of the cam, and a crank operatively connected to the cam follower for swinging movement with rocking of the cam follower, the crank being pivotally mounted to the thigh member and being operatively connected to the shank member for pivoting the shank member about the knee joint with rotation of the cam.

4. A powered gait orthosis according to claim 3, wherein said knee drive means includes a rocker pivotally mounted to the thigh member and carrying the cam follower, and a cable connected between the rocker and the crank.

5. A powered gait orthosis according to claim 4, wherein said knee drive means includes a shank lever connected to and extending rearwardly of the shank member, and a floating link pivotally connected between the crank and the shank lever.

6. A powered gait orthosis according to claim 4, wherein said automatic knee joint lock comprises a lock shoulder on one or the shank member and crank, and a lock projection on the other of the shank member and crank for engaging on the lock shoulder when the shank member is pivoted on the knee joint to extend approximately parallel to the thigh member.

7. A powered gait orthosis according to claim 4, including a return spring engaged between the thigh member and the shank member for pivoting the shank member forwardly on the knee joint with respect to the thigh member.

8. A powered gait orthosis according to claim 1, including a power unit mounted to the torso member, said power unit being engaged to said hip drive means and to said knee drive means for activating said hip and knee drive means to move the thigh and shank members about the respective hip and knee joints.

9. A powered gait orthosis according to claim 1, including manual release means connecting said hip drive means to said thigh member for manually disengaging said hip drive means from said thigh member to permit the thigh member to pivot freely about the hip joint with respect to the torso member.

10. A powered gait orthosis according to claim 1, including manual knee joint release means connected between said knee drive means and said shank member for manually disconnecting said knee drive means from the shank member for allowing free pivotal movement of the shank member about the knee joint with respect to the thigh member.

11. A powered gait orthosis according to claim 1, wherein said hip drive means comprises a link pivotally mounted at a rotation axis to the thigh member, the rotation axis being spaced above the hip joint with the torso member extending upright, said link engaged to the thigh member for pivoting the thigh member forwardly and rearwardly with rotation of the link, said knee drive means comprising a cam connected to the link, a cam follower movably mounted to the thigh member and engaged with an outer surface of the cam for rocking movement of the cam follower with rotation of the cam, a crank pivotally mounted to the thigh member and engaged with the cam follower for swinging movement of the crank, a floating connection between the crank and the shank member for swinging the shank member rearwardly on the knee joint with respect to the thigh member when the crank moves, said automatic knee joint lock being defined between the crank and an upper end of the shank member adjacent to the knee joint for locking the knee joint when the shank member is substantially parallel to the thigh member.

12. A powered gait orthosis according to claim 11, including return means engaged between the thigh member and the shank member for pivoting the shank member on the knee joint toward a position which is parallel to the thigh member.

13. A method of powering the gait of a person with impaired walking ability, comprising:
    firmly connecting torso members to the opposite sides of the person's torso;
    firmly connecting thigh members to each upper leg of the person, each thigh member being pivotally connected to one of the torso members at a hip joint;
    firmly connecting shank members to each lower leg of the person, each shank member being pivotally connected to one of the thigh members at a knee joint;
    providing a motor driven means for powering the forward and rearward swinging of the high members in synchronized opposite directions located on the respective torso members and connected to the respective thigh members;
    providing a means, connected to a driver by said motor driver means for locking each knee joint to preclude pivotal movement of each shank member with respect to each respective thigh member, during rearward pivotal movement of each thigh member and up to a selected point during forward movement of each thigh member;
    at the selected point of forward movement of each thigh member, unlocking each knee joint with same said means for locking and powering a rearward pivoting of each shank member about the respective knee joint; and
    at a point of substantial maximum forward movement of each respective thigh member, pivoting each respective shank member forwardly and locking each respective knee joint in preparation of a subsequent rearward swing of each respective thigh member.

14. A method according to claim 13, including powering the forward and rearward swinging of each respective thigh member using a four link drive connected between each torso member and each respective thigh member.

15. A method according to claim 14, including powering the rearward pivoting of each respective shank member using a cam which is rotatably mounted to each respective torso member, a cam follower engaged with each respective cam, a crank pivotally mounted to each respective thigh member and connected to each respective cam follower by a cable and a floating link connected between each crank and each respective shank member.

16. A method according to claim 15, including swinging each respective shank member forwardly about each respective knee joint using a spring connected between each shank member and each respective thigh member.

17. A method according to claim 16 wherein the cam and the four link drive mechanism are drive by a rechargeable battery operated motor and gear box mounted to each of the torso members.

* * * * *